(12) United States Patent
Hill et al.

(10) Patent No.: US 6,417,000 B1
(45) Date of Patent: Jul. 9, 2002

(54) CARBOXYLATE-SULFONATE POLYMERS

(75) Inventors: Frank Hill, deceased, late of Mettmann, by Hella Luise Hill, Henning Hinrich Hill, executors; by Friedrich Frank Hill, Waldsee; by Regina Luise Hill, Speyer; Peter Ottersbach, Windeck, all of (DE); Graciella Djavid, Paris (FR); Marcel Jozefowicz, Lamorlaye (FR); Veronique Migonney, Eaubonne (FR); Jean-Pierre Vairon, Bonzy la Reine (FR)

(73) Assignee: Le Groupement d'Intérét Public Thérapeutiques Substitutives Institut Galilée, Université Paris-Nord, Villetaneuse (FR)

( * ) Notice: Subject to any disclaimer, the term of this patent is extended or adjusted under 35 U.S.C. 154(b) by 0 days.

(21) Appl. No.: 09/999,295

(22) Filed: Nov. 15, 2001

Related U.S. Application Data

(62) Division of application No. 09/001,143, filed on Dec. 30, 1997.

(30) Foreign Application Priority Data

Jan. 3, 1997 (DE) .......................................... 197 00 078

(51) Int. Cl.$^7$ ................................................ C12N 5/00
(52) U.S. Cl. ...................................... 435/396; 435/402
(58) Field of Search ................................. 435/396, 402

(56) References Cited

U.S. PATENT DOCUMENTS

| | | |
|---|---|---|
| 4,056,517 A | 11/1977 | Albers |
| 5,278,200 A | 1/1994 | Coury et al. |
| 5,756,625 A | 5/1998 | Crandall |

FOREIGN PATENT DOCUMENTS

| | | |
|---|---|---|
| EP | 0 290 642 A1 | 11/1988 |
| EP | 0 093 489 A2 | 11/1993 |
| EP | 0 604 369 A1 | 6/1994 |
| JP | 030703 | 2/1982 |
| JP | 036309 | 2/1986 |
| WO | WO 90/02145 | 3/1990 |
| WO | WO 96/39821 | 12/1996 |

OTHER PUBLICATIONS

Hans Beyer, et al., S. Hirzel Verlag Stuttgart, pp. 260–265, 1988, "Textbook of Organic Chemistry".

Hans–Georg Elias, Huethig & Wepf Verlag, Heidelberg, pp. 600–616, 1981, "Macromolecules".

Gerhard Mueller, et al., Angewandte Chemie, vol. 104, pp. 341–343, 1992, "Dynamischer Zwang, Eine Helfe Fuer Das Verstaendnis Der Aktivitaet Und Selektivitaet Von Rgd (Arg–Gly–Asp)–Peptiden".

*Primary Examiner*—Christopher Henderson
(74) *Attorney, Agent, or Firm*—Alson & Bird LLP

(57) ABSTRACT

The invention relates to water-insoluble polymers which promote cell proliferation, contain carboxylate and sulfonate groups and are obtainable by free radical copolymerization of one or more aliphatically unsaturated monomers containing carboxylate groups, or the correspondingly functionalized derivatives of the monomers, as component I with one or more aliphatically unsaturated monomers containing sulfonate groups, or the correspondingly functionalized derivatives of the monomers, as component II and a component III which comprises an aliphatically unsaturated monomer or several aliphatically unsaturated monomers, the correspondingly functionalized derivatives being converted into carboxylate and sulfonate groups after the copolymerization, and to a process for their preparation, wherein the polymers are useful for forming articles which promote cell proliferation.

14 Claims, No Drawings

CARBOXYLATE-SULFONATE POLYMERS

CROSS-REFERENCE TO RELATED APPLICATIONS

This application is a divisional of U.S. Application Ser. No. 09/001,143, filed Dec. 30, 1997, which is incorporated herein in its entirety by reference.

BACKGROUND OF THE INVENTION

1. Field of the Invention

The invention relates to water-insoluble polymers which promote cell proliferation and to a process for their preparation. The invention furthermore relates to the use of the water-insoluble polymers which promote cell proliferation for the production of products having a surface which promotes cell proliferation and for the production of products having a coating, of the polymer, which promotes cell proliferation. The invention moreover relates to products having a surface which promotes cell proliferation and products having a coating, of the polymer, which promotes cell proliferation. For numerous medical applications of materials such as polymers, ceramics and metals, for example as suture materials, stems, implants or prostheses, good compatibilities with the immune and complement system and the blood must be ensured. This property, which is often called biocompatibility, includes avoidance of degradation phenomena of the materials by physiological components, such as enzymes and macrophages.

2. Description of the Prior Art

An improved biocompatibility of substitute materials employed medically can be achieved in principle by colonization with human cells. The process described in EP 0 290 642 initially requires covalent bonding of an intermediate layer of so-called copolymers onto polymer surfaces functionalized by carboxyl, amino and hydroxyl groups. The biocompatibility sought in the material is then achieved by careful, extracorporeal colonization of the intermediate layer with endothelial cells.

WO 90/02145 describes, with the same aim, a process in which acrylic acid is grafted onto fluorine-containing polymer substrates by irradiation with a $^{60}$Co source or a laser. After a series of chemical processes on the surface, controlled absorption of proteins takes place, which is followed by colonization with endothelial cells to establish the biocompatibility.

These processes are extremely time-consuming and cost-intensive and require the greatest care for a medical application, so that the endothelial cell layers applied extracorporeally are not damaged. It is furthermore not possible to allow the cell colonization and cell growth (cell proliferation) to be carried out by the body itself in vivo, since an undesirable thrombic reaction starts before the cell colonization.

Subsequent chemical modification of surfaces of polymeric materials with the known RGD sequence method (arginine-glycine-aspartic acid) is usually not uniform and/or standard. Untreated areas often remain, which are no longer available as starting points for cell colonization of the surface (G. Muller, Angewandte Chemie, 104 (1992) 341 et seq.).

From another technical field, according to U.S. Pat. No. 5,278,200, polymers which contain carboxylate and sulfonate groups in a ratio comparable to that of naturally occurring heparin are known. These polymers have anticoagulating properties with respect to platelets in the blood.

SUMMARY OF THE INVENTION

The present invention is therefore based on the object of improving cell proliferation on the surfaces of polymers. It has now been found, surprisingly, that water-insoluble polymers which contain carboxylate and sulfonate groups and are obtainable by free radical copolymerization of

- one or more aliphatically unsaturated monomers containing carbox ylate groups, or the correspondingly functionalized derivatives of the monomers, as component I with
- one or more aliphatically unsaturated monomers containing sulfonate groups, or the correspondingly functionalized derivatives of the monomers, as component II and
- a component III which comprises an aliphatically unsaturated monomer or several aliphatically unsaturated monomers, the correspondingly functionalized derivatives being converted into carboxylate and sulfonate groups after the copolymerization, are capable of promoting cell proliferation.

The adhesion and the growth of cells is thus improved in a physiologically tolerated manner on the polymers according to the invention.

The polymers according to the invention are thus particularly suitable for the production of implants in which growth of endogenous or non-differentiated cells is desired.

The present invention therefore relates to water-insoluble polymers which promote cell proliferation, contain carboxylate and sulfonate groups and are obtainable by free radical copolymerization of

- one or more aliphatically unsaturated monomers containing carbox ylate groups, or the correspondingly functionalized derivatives of the monomers, as component I with
- one or more aliphatically unsaturated monomers containing sulfonate groups, or the correspondingly functionalized derivatives of the monomers, as component II and
- a component III which comprises an aliphatically unsaturated monomer or several aliphatically unsaturated monomers, the correspondingly functionalized derivatives being converted into carboxylate and sulfonate groups after the copolymerization.

The present invention furthermore relates to a process for the preparation of water-insoluble polymers, which promote cell proliferation and contain carboxylate and sulfonate groups, which comprises obtaining the polymers by free radical copolymerization of one or more aliphatically unsaturated monomers containing carboxylate groups, or the correspondingly functionalized derivatives of the monomers, as component I with one or more aliphatically unsaturated monomers containing sulfonate groups, or the correspondingly functionalized derivatives of the monomers, as component II and a component III which comprises an aliphatically unsaturated monomer or several aliphatically unsaturated monomers, the correspondingly functionalized derivatives being converted into carboxylate and sulfonate groups after the copolymerization.

The present invention moreover relates to the use of the water-insoluble polymers, which promote cell proliferation and contain carboxylate and sulfonate groups, for the production of products having a surface which promotes cell proliferation, and to the use of the water-insoluble polymers, which promote cell proliferation and contain carboxylate and sulfonate groups, for the production of products having a coating, of the polymer, which promotes cell proliferation.

The present invention furthermore relates to the use of the water-insoluble polymers, which promote cell proliferation and contain carboxylate and sulfonate groups, for the production of medical articles, in particular artificial blood vessels, having a surface which promotes cell proliferation.

The present invention moreover relates to the use of the water-insoluble polymers, which promote cell proliferation and contain carboxylate and sulfonate groups, for the production of medical articles of plastics, ceramics or metals having a coating, of the polymer, which promotes cell proliferation.

The present invention furthermore relates to the use of the water-insoluble polymers, which promote cell proliferation and contain carboxylate and sulfonate groups, for the production of artificial blood vessels having a coating, of the polymer, which promotes cell proliferation.

The present invention also relates to products having a surface, which promotes cell proliferation, of water-insoluble polymers, which promote cell proliferation and contain carboxylate and sulfonate groups.

Such products according to the invention are preferably medical articles, particularly preferably artificial blood vessels.

The present invention also relates to products having a coating, which promotes cell proliferation, of water-insoluble polymers, which promote cell proliferation and contain carboxylate and sulfonate groups.

Products having a coating, of the polymer according to the invention, which promotes cell proliferation are preferably medical articles, particularly preferably medical articles of plastics, ceramics or metals. Medical articles having a coating, of the polymer according to the invention, which promotes cell proliferation are preferably artificial blood vessels.

DESCRIPTION OF THE PREFERRED EMBODIMENTS

The polymers according to the invention are prepared by copolymerization of three components. For the polymers according to the invention and for the process according to the invention, an aliphatically unsaturated monomer containing carboxylate and sulfonate groups or several aliphatically unsaturated monomers containing carboxylate and sulfonate groups or the correspondingly functionalized derivatives of the monomers can also be employed as component I.

For the polymers according to the invention and for the process according to the invention, an aliphatically unsaturated monomer containing carboxylate and sulfonate groups or several aliphatically unsaturated monomers containing carboxylate and sulfonate groups or the correspondingly functionalized derivatives of the monomers can furthermore also be employed as component II.

In a particular embodiment of the present invention, component I can be identical to component II for the polymers according to the invention and for the process according to the invention.

The aliphatically unsaturated monomers to be employed for the polymers according to the invention can contain both double bonds and triple bonds. The monomers preferably have one or two double bonds.

For the introduction of carboxylate groups into the polymers according to the invention, all polymerizable compounds of the formula 1), or mixtures thereof, which carry carboxylate groups are suitable, for example, as component 1, such as, for example

  1)

where

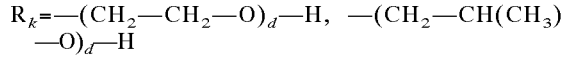

or

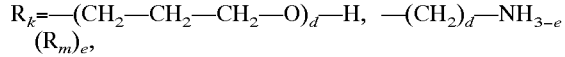

where

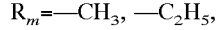

d=0, 1, 2, 3 or 4, e=0, 1, 2 or 3, n=2, 3, 4, 5 or 6, q=0 or 2 and x=1 or 2.

The ester groups are hydrolyzed after the polymerization and are thus present in ionic form. The aliphatically unsaturated monomers can be both straight-chain and branched.

Monomer components which can be derived from benzene, of the empirical formula $(C_6H_{6-a-b-c})A_aB_b(OH)_c,$ are also suitable for the preparation of the polymers according to the invention, for example as component I, in which $A=(C_nH_{2n-q-x-1})(COOR_k)_x$ where

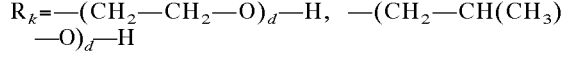

or

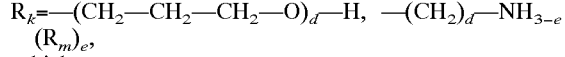

in which

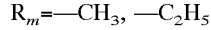

a=0, 1, 2 or 3, b=0, 1, 2 or 3, c=0, 1, 2 or 3, d=0, 1, 2, 3 or 4, e=0, 1, 2 or 3, n=2, 3, 4, 5 or 6, q=1 or 2, x=0, 1 or 2 and

B=—COOH, —SO$_3$H, —NH$_2$, —N$^+$(CH$_3$)$_3$, —O—PO$_3$H$^-$ or —OSO$_3$H or

B=—O—PO$^-_2$—O—CH$_2$—CH$_2$—N$^+$(CH$_3$)$_3$.

Sulfonate groups can be introduced into the polymers according to the invention with the following compounds of the formula 2) or mixtures thereof as component II:

  2)

where

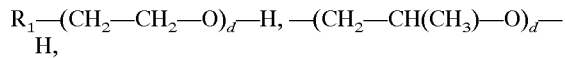

or

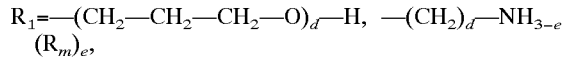

in which $R_m$=—$CH_3$, —$C_2H_5$, d=0, 1, 2, 3 or 4, e=0, 1, 2 or 3,

M=0, 2, 3, 4, 5 or 6, s=0 or 2, and y=1 or 2.

The ester groups are hydrolyzed after the polymerization and are thus present in ionic form. The aliphatically unsaturated monomers can be both straight-chain and branched.

Monomer components which can be derived from benzene, of the empirical formula $$(C_6H_{6-k-i-p})K_kL_i(OH)_p,$$

can also be employed for the preparation of the polymers according to the invention, for example as component II, in which $$K=(C_mH_{2m-s-y-1})(SO_3R_1)_y,$$

in which d=0, 1, 2, 3 or 4, e=0, 1, 2, or 3, i=0, 1, 2 or 3, k=0, 1, 2 or 3, m=0, 2, 3, 4, 5 or 6, p=0, 1, 2 or 3, s=0 or 2, y=0, 1 or 2, and

L=—COOH, —$SO_3H$, —$NH_2$, —$N^+(CH_3)_3$, —O—$PO_3H^-$, —$OSO_3H$ or

L=—O—$PO^-_2$—O—$CH_2$—$CH_2$—$N^+(CH_3)_3$.

The sum of the proportions of component I and component II for the polymers according to the invention and for the process according to the invention is preferably 5 to 30 mol %, particularly preferably 15 to 20 mol %.

For the polymers according to the invention and for the process according to the invention, the ratio of the carboxylate groups to sulfonate groups contained in the polymer is 3 to 10, particularly preferably 3 to 5.

The copolymerization of the above-mentioned monomers as components I and II is carried out according to the invention with one or more other aliphatically unsaturated monomers as component III.

A monomer which carries nonionic groups is preferably used as component III. These monomers include, for example, vinyl compounds, allyl compounds, acrylic compounds, olefins, dienes, unsaturated halogeno hydrocarbons and correspondingly functionalized derivatives thereof.

The polymers according to the invention can be prepared, for example, with the aid of emulsion polymerization according to the prior art (Hans-Georg Elias, Makromoleküle [Macromolecules], Hüthig & Wepf Verlag, Heidelberg, 1981, p. 603 et seq.).

For the preparation of the polymers according to the invention, components I, II and III can furthermore also be copolymerized in solution or in bulk by the known processes. (Hans-Georg Elias, Makromoleküle [Macromolecules], Hüthig & Wepf Verlag, Heidelberg, 1981, p. 602 et seq.).

The following solvents, for example, can be employed for copolymerization of components I, II and III in solution: water, acetone, methyl ethyl ketone, butanone, cyclohexanone, diethyl ether, tetrahydrofuran, dioxane, methanol, ethanol, propanol, butanol, cyclohexanol, dimethylacetamide, dimethyl sulfoxide, dimethylformamide, heptane, cyclohexane, benzene, toluene, dichloromethane, trichloromethane, ethyl acetate, propyl acetate, amyl acetate and acetonitrile, Azonitriles, alkyl peroxides, acyl peroxides, hydroperoxides, peroxoketones, peresters and peroxocarbonates, peroxodisulfate, persulfate and all customary photoinitiators can be used, inter alia, as polymerization initiators. The polymerization can be initiated by heat or by electromagnetic radiation, such as, for example, UV light or γ-radiation.

If no monomers containing carboxylate and/or sulfonate groups but instead functionalized derivatives thereof, such as, for example, a carboxylic acid ester instead of a carboxylic acid, are used for the preparation of the polymers according to the invention, the functionalized derivatives must be converted into carboxylate or sulfonate groups after the polymerization. In the case of the carboxylic acid ester, this can be carried out by means of base-catalyzed hydrolysis. The derivatization of polymeric materials can be carried out by generally known processes (Hans Beyer, Lehrbuch der organischen Chemie [Textbook of organic chemistry], S. Hirzel Verlag, Stuttgart, 1988, p. 260 et seq.).

Products having a surface which promotes cell proliferation can be produced directly from the polymers according to the invention. However, the polymers according to the invention can also be applied, if appropriate as solutions in suitable solvents, as thin layers to standard polymers by application techniques such as spraying, painting, dipping, knife-coating or coating or by multilayer injection molding, coextrusion or calendering and lamination.

Fixing of the polymers according to the invention on standard polymers, which are activated if appropriate, by primer layers or intermediate layers of bifunctional compounds is furthermore possible.

Such standard polymers are, for example, PVC, polystyrene, polyurethanes, polyacrylates, polymethacrylates, polyesters, polyethers, polyether-block amides, polyamides, polycarbonates, polyolefins, silicones and polytetrafluoroethylene.

The measurement method for determination of the cell proliferation is described below.

Preparation of the cell suspension.

Human fibroblasts of the cell line ATCC CRL1696 (American Type Culture Collection, Rockville, Md., USA) are cultured in DMEM (Dulbecco's Modified Eagles Medium) with the addition of antibiotics, L-glutamine and 10% of a fetal calf serum in culture bottles at 37° C. under an atmosphere of 5% $CO_2$ and 95% air. After incubation, the nutrient medium is removed and the cell lawn is treated with 0.05% trypsin/0.02% EDTA for 5 minutes. The cells are then washed with DMEM and suspended in the same nutrient medium.

Measurement of the cell proliferation.

In a 250 ml conical flask, a polymer sample 2×2 cm in size is pricked onto a dissecting needle and sterilized with ethylene oxide, and 20 ml of the above-mentioned nutrient medium are added. The polymer sample is then inoculated with $10^5$ cells from the freshly prepared cell suspension and incubated for 8 days. The polymer sample is removed and rinsed with sterile PBS buffer solution. The adenosine triphosphate is then extracted from the cells with the aid of hot Tris/EDTA solution and determined quantitatively with the bioluminescence reagent CLSII (Boehringer Mannheim GmbH, Mannheim).

Samples which were obtained by polymerization of component III of the particular polymer according to the invention and were prepared in the same manner were used as reference sample. In a control experiment, a polymer sample was rinsed immediately after inoculation with the cell suspension and the cells rinsed off were determined quantitatively by the method described above. The promotion of cell proliferation is expressed as the percentage quotient of the ATP concentration of the cells which have grown on the polymers according to the invention divided by the corresponding value of the reference sample.

The measurement results given in the following examples show that the cell proliferation increases between 60% and 110% on polymers according to the invention.

The following examples are intended to illustrate the invention in more detail. These examples are set forth by way of illustration only, and nothing therein shall be taken as a limitation upon the overall scope of the invention.

EXAMPLES

Preparation of samples of the polymers according to the invention.

Example 1

223.2 g of methyl methacrylate, 12.1 g of methacrylic acid and 4.9 g of sodium styrenesulfonate are dissolved in 500 ml of dimethyl sulfoxide in a nitrogen atmosphere. The solution is heated to 70° C., while stirring. 2.3 g of azobisisobutyronitrile, dissolved in 30 ml of dimethyl sulfoxide, are then added dropwise in the course of 2 minutes. The polymerization is carried out at 70° C. over a period of 16 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Methacrylic acid: 14 mol %

Sodium styrenesulfonate: 4 mol %

Methyl methacrylate: 82 mol %

A ratio of carboxylate groups to sulfonate groups of 3.5 results from these values.

Example 2

201.6 g of methyl methacrylate, 25.9 g of acrylic acid and 4.9 g of sodium styrenesulfonate are dissolved in 500 ml of dimethyl sulfoxide in a nitrogen atmosphere. The solution is heated to 70° C., while stirring. 2 g of azobisisobutyronitrile, dissolved in 30 ml of dimethyl sulfoxide, are then added dropwise in the course of 2 minutes. The polymerization is carried out at 70° C. over a period of 16 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Acrylic acid: 18 mol %

Sodium styrenesulfonate: 5 mol %

Methyl methacrylate: 77 mol %

A ratio of carboxylate groups to sulfonate groups of 3.6 results from these values.

Example 3

244.0 g of styrene, 2.6 g of methacrylic acid and 4.9 g of sodium styrenesulfonate are dissolved in 500 ml of dimethyl sulfoxide in a nitrogen atmosphere. The solution is heated to 70° C., while stirring. 2.3 g of azobisisobutyronitrile, dissolved in 30 ml of dimethyl sulfoxide, are then added dropwise in the course of 2 minutes. The polymerization is carried out at 70° C. over a period of 20 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Methacrylic acid: 10 mol %

Sodium styrenesulfonate: 3 mol %

Styrene: 87 mol %

A ratio of carboxylate groups to sulfonate groups of 3.3 results from these values.

Example 4

225 g of styrene, 14.2 g of acrylic acid and 9.9 g of sodium styrenesulfonate are dissolved in 500 ml of dimethyl sulfoxide in a nitrogen atmosphere. The solution is heated to 70° C., while stirring. 2.3 g of azobisisobutyronitrile, dissolved in 30 ml of dimethyl sulfoxide, are then added dropwise in the course of 2 minutes. The polymerization is carried out at 70° C. over a period of 20 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Acrylic acid: 21 mol %

Sodium styrenesulfonate: 5 mol %

Styrene: 74 mol %

A ratio of carboxylate groups to sulfonate groups of 4.2 results from these values.

Example 5

316.3 g of n-butyl methacrylate, 12.5 g of methacrylic acid and 4.9 g of sodium styrenesulfonate are dissolved in 500 ml of dimethyl sulfoxide in a nitrogen atmosphere. The solution is heated to 70° C., while stirring. 2.3 g of azobisisobutyronitrile, dissolved in 30 ml of dimethyl sulfoxide, are then added dropwise in the course of 2 minutes. The polymerization is carried out at 70° C. over a period of 20 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Methacrylic acid: 16 mol %

Sodium styrenesulfonate: 4 mol % n-Butylmethacrylate: 81 mol %

A ratio of carboxylate groups to sulfonate groups of 4.0 results from these values.

Example 6

317 g of n-butyl methacrylate, 11.2 g of acrylic acid and 2.5 g of sodium styrenesulfonate are dissolved in 500 ml of dimethyl sulfoxide in a nitrogen atmosphere. The solution is heated to 70° C., while stirring. 2.3 g of azobisisobutyronitrile, dissolved in 30 ml of dimethyl sulfoxide, are then added dropwise in the course of 2 minutes. The polymerization is carried out at 70° C. over a period of 16 hours. Thereafter, the product which has formed is precipitated in a fourfold excess of ice-water, subsequently extracted in a Soxhlet with water for 24 hours and dried at 50° C. in vacuo.

Subsequent analysis of the composition by $^1$H-NMR gives:

Acrylic acid: 9 mol %

Sodium styrenesulfonate: 2 mol % n-Butyl methacrylate: 89 mol %

A ratio of carboxylate groups to sulfonate groups of 4.5 results from these values.

Production of membranes from polymers according to the invention.

Example 7

A 5% strength dimethyl sulfoxide solution of the polymers according to the invention according to Examples 1, 2 and 5 is prepared. The solution is poured into a Petri dish and the solvent is removed from the sample at 80° C. under reduced pressure. The membrane thus produced is then broken up into pieces of 2 cm×2 cm each and extracted with water for 24 hours. Before the subsequent biological analyses, the membrane pieces are washed in a Michaelis buffer solution (pH=7.33) three times for three hours each time and stored at −4° C. until analyzed further.

Production of coatings of polymers according to the invention

Example 8

A 5% strength methyl ethyl ketone solution of the polymer according to the invention according to Example 3 is prepared. A polyamide film 10 cm×8 cm×0.04 cm in size is dipped into this solution for 10 seconds. The film is removed and dried at 50° C. under reduced pressure for 10 hours. The film coated with the polymer according to the invention is then broken up into pieces of 2 cm×2 cm each and extracted with water for 24 hours. Before the subsequent biological analyses, the samples are washed in a Michaelis buffer solution (pH=7.33) three times for three hours each time and kept at −4° C. until analyzed further.

Example 9

A 5% strength acetone solution of the polymer according to the invention according to Example 4 is prepared. A polyethylene film 10 cm×8 cm×0.03 cm in size, the surface of which has been activated beforehand by irradiation with the 172 nm radiation of an excimer emitter for 3 minutes, is immersed in this solution for 15 seconds. The film is removed and dried at 50° C. under reduced pressure for 10 hours. The coated film is then broken up into pieces of 2 cm×2 cm each and extracted with water for 24 hours. Before the subsequent biological analyses, the samples are washed in a Michaelis buffer solution (pH=7.33) three times for three hours each time and kept at −4° C. until analyzed further.

Example 10

A 5% strength acetone solution of the polymer according to the invention according to Example 6 is prepared. A polyether-block-amide film 10 cm×8 cm×0.04 cm in size is immersed in this solution for 10 seconds. The film is removed and dried at 50° C. under reduced pressure for 10 hours. The coated film is then broken up into pieces of 2 cm×2 cm each and extracted with water for 24 hours. Before the subsequent biological analyses, the samples are washed in a Michaelis buffer solution (pH=7.33) three times for three hours each time and kept at −4° C. until analyzed further.

Conditioning of the samples of polymers according to the invention.

Example 11

The membranes according to Example 7 and the films according to Examples 8 to 10 coated with the polymers according to the invention are sterilized by irradiation with ultraviolet light for 15 minutes. The samples pretreated in this way are then kept in a 0.15 molar sodium chloride solution three times for three hours each time and then washed with distilled water for 3 hours. In the subsequent purification step, they are placed in a phosphate buffer solution of the following composition three times for three hours each time:

| | |
|---|---|
| $CaCl_2.H_2O$ | 0.132 g/l |
| KCl | 0.2 g/l |
| $KH_2PO_4$ | 0.2 g/l |
| $MgCl_2.6H_2O$ | 0.1 g/l |
| NaCl | 8 g/l |
| $Na_2HPO_4$ | 1.15 g/l |

Thereafter, the samples are irradiated with ultraviolet light again for 15 minutes. The samples thus present are kept in a DMEM solution (Dulbecco's Modified Eagles Medium) at 37° C. for about 16 hours. Finally, the samples are kept in a DMEM solution, to which antibiotics, L-glutamine and 10% by volume of a fetal calf serum have been added, at 37° C. under an atmosphere of 5% $CO_2$ and 95% air for a further 16 hours.

The polymers according to the invention produced according to Examples 1, 2 and 5 were processed to membranes (Example 7). Polymers according to the invention according to Examples 3, 4 and 6 were applied to standard polymers (Examples 8 to 10). These samples were then conditioned according to Example 11 and the cell proliferation was determined by the process described.

The following table shows the relative colonization of the polymers according to the invention by human fibroblasts.

| Polymer according to the invention according to Example | Reference polymer | Relative colonization in % (reference polymer = 100) |
|---|---|---|
| 1 | Polymethyl methacrylate | 165 |
| 2 | Polymethyl methacrylate | 181 |
| 3 | Polystyrene | 161 |
| 4 | Polystyrene | 217 |
| 5 | Poly-n-butyl methacrylate | 173 |
| 6 | Poly-n-butyl methacrylate | 162 |
| Control sample, t = 0 h | Polystyrene | 1.8 |

Obviously, numerous modifications and variations of the present invention are possible in light of the above teachings. It is therefore to be understood that within the scope of the appended claims, the invention may be practiced otherwise than as specifically described herein.

This application is based upon German patent Application No. 197 00 078.9 filed with the German Patent Office on Jan. 3, 1997, the entire contents of which are herein incorporated by reference.

What is claimed as new and desired to be secured by Letters Patent of the United States is:

1. A method for promoting cell proliferation on the surface of a polymer, wherein said polymer is water-insoluble, contains carboxylate groups and sulfonate groups, and is produced by free-radical copolymerization of component I, component II and component III, wherein:

component I comprises an aliphatically unsaturated monomer containing a carboxylate group or a substituent that is capable of being converted into a carboxylate group, the latter being converted into the carboxylate group after the copolymerization;

component II comprises an aliphatically unsaturated monomer containing a sulfonate group or a substituent that is capable of being converted into a sulfonate group, the latter being converted into the sulfonate group after the copolymerization;

component III comprises an aliphatically unsaturated monomer.

2. The method according to claim 1, wherein component I further comprises an aliphatically unsaturated monomer containing a sulfonate group or a substituent that is capable of being converted into a sulfonate group, the latter being converted into the sulfonate group after copolymerization.

3. The method according to claim 1, wherein component II further comprises an aliphatically unsaturated monomer containing a carboxylate group or a substituent that is capable of being converted into a carboxylate group, the latter being converted into the carboxylate group after the copolymerization.

4. The method according to claim 1, wherein component I and component II are identical.

5. The method according to claim 1, wherein from 5 to 30 mol % of the polymer is derived from component I and component II.

6. The method according to claim 1, wherein from 15 to 20 mol % of the polymer is derived from component I and component II.

7. The method according to claim 1, wherein the ratio of carboxylate groups to sulfonate groups contained in the polymer is 3 to 10.

8. The method according to claim 1, wherein the ratio of carboxylate groups to sulfonate groups contained in the polymer is 3 to 5.

9. The method according to claim 2, wherein component I responds to the formula $(C_nH_{2n-q-x})(COOR_k)_x$, wherein:

$R_k$=—$(CH_2$—$CH_2$—$O)_d$—H, —$(CH_2$—$CH(CH_3)$—$O)_d$—H, —$(CH_2$—$CH_2$—$CH_2$—$O)_d$—H or —$(CH_2)_d$—$NH_{3-e}(R_m)_e$, $R_m$=—$CH_3$ or —$C_2H_5$, d=0, 1, 2, 3 or 4, e=0, 1, 2 or 3, n=2, 3, 4, 5 or 6, q=0 or 2, x=1 or 2.

10. The method according to claim 1, wherein component I responds to the formula $(C_6H_{6-a-b-c})A_aB_b(OH)_c$, wherein:

A=$(C_nH_{2n-q-x-1})(COOR_k)_x$, $R_k$=—$(CH_2$—$CH_2$—$O)_d$—H, —$(CH_2$—$CH(CH_3)$—$O)_d$—H, —$(CH_2$—$CH_2$—$CH_2$—$O)_d$—H or —$(CH_2)_d$—$NH_{3-e}(R_m)_e$, $R_m$=—$CH_3$ or —$C_2H_5$, a=0, 1, 2 or 3, b=0, 1, 2 or 3, c=0, 1, 2 or 3, d=0, 1, 2, 3 or 4, e=0, 1, 2 or 3, n=2, 3, 4, 5 or 6, q=1 or 2, x=0, 1, or 2,

B=—COOH, —$SO_3H$, —$NH_2$, —$N^+(CH_3)_3$, —O—$PO_3H^-$, —$OSO_3H$, —O—$PO^-_2$—O—$CH_2$—$CH_2$—$N^+(CH_3)_3$.

11. The method according to claim 1, wherein component II responds to the formula $(C_mH_{2m-s-y})(SO_3R_1)_y$, wherein:

$R_1$—$(CH_2$—$CH_2$—$O)_d$—H, —$(CH_2$—$CH(CH_3)$—$O)_d$—H, —$(CH_2$—$CH_2$—$CH_2$—$O)_d$—H or —$(CH_2)_d$—$NH_{3-e}(R_m)_e$, $R_m$—$CH_3$ or —$C_2H_5$, d=0, 1, 2, 3 or 4, e=0, 1, 2 or 3, m=2, 3, 4, 5 or 6, s=0 or 2 y=1 or 2.

12. The method according to claim 1, wherein component II responds to the formula $(C_6H_{6-k-i-p})K_kL_i(OH)_p$, wherein:

K=$(C_mH_{2m-s-y-1}))(SO_3R_1)_y$, d=0, 1, 2, 3 or 4, e=0, 1, 2 or 3, i=0, 1, 2 or 3, k=0, 1, 2 or 3, m=0, 2, 3, 4, 5 or 6, p=0, 1, 2 or 3, s=0 or 2, y=0, 1 or 2, y=0, 1 or 2,

L=—COOH, —$SO_3H$, —$NH_2$, —$N^+(CH_3)_3$, —O—$PO_3H^-$, —$OSO_3H$, —O—$PO^-_2$—O—$CH_2$—$N^+(CH_3)_3$.

13. The method according to claim 1, wherein component if is chosen from vinyl, allyl or acrylic compounds, olefins, dienes, unsaturated halogeno hydrocarbons and functionalized derivatives thereof.

14. The method according to claim 1, wherein component I is chosen from acrylic acid and methacrylic acid, component I is sodium styrenesulfonate and component III is chosen from methylmethacrylate, n-butylmethacrylate and styrene.

* * * * *

UNITED STATES PATENT AND TRADEMARK OFFICE
CERTIFICATE OF CORRECTION

PATENT NO.     : 6,417,000 B1
DATED          : July 9, 2002
INVENTOR(S)    : Hill et al.

It is certified that error appears in the above-identified patent and that said Letters Patent is hereby corrected as shown below:

Title page, Item [54] and Column 1, line 1,
Title, "CARBOXYLATE-SULFONATE POLYMERS" should read
-- USE OF CARBOXYLATE-SULFONATE POLYMERS HAVING CELL PROLIFERATION-PROMOTING PROPERTIES --.

Item [56], References Cited, OTHER PUBLICATIONS,
"Helfe" should read -- Hilfe --.

Item [74], *Attorney, Agent, or Firm*, "Alson" should read -- Alston --.

Column 4,
Line 63, after "$R_1$" insert -- = --.

Column 11,
Line 58, "claim 2" should read -- claim 1 --.

Column 12,
Line 28, after "$R_1$" insert -- = --;
Line 31, after "$R_m$" insert -- = --.
Line 58, "if" should read -- III --.

Signed and Sealed this

Nineteenth Day of November, 2002

*Attest:*

*Attesting Officer*

JAMES E. ROGAN
*Director of the United States Patent and Trademark Office*